(12) United States Patent
DiDomenico et al.

(10) Patent No.: US 6,983,639 B1
(45) Date of Patent: Jan. 10, 2006

(54) REMOTE EMISSIONS SENSING SYSTEM WITH IMPROVED $NO_X$ DETECTION

(75) Inventors: John DiDomenico, Tucson, AZ (US);
Craig S. Rendahl, Marana, AZ (US);
James Johnson, Tucson, AZ (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 853 days.

(21) Appl. No.: 09/709,935

(22) Filed: Nov. 13, 2000
(Under 37 CFR 1.47)

Related U.S. Application Data

(63) Continuation of application No. 09/520,166, filed on Mar. 7, 2000, now abandoned, which is a continuation of application No. 09/398,199, filed on Sep. 17, 1999, now abandoned.

(60) Provisional application No. 60/100,913, filed on Sep. 17, 1998.

(51) Int. Cl.
*G01N 7/00* (2006.01)

(52) U.S. Cl. ..................................... 73/23.31
(58) Field of Classification Search ................ 73/23.31
See application file for complete search history.

(56) References Cited

U.S. PATENT DOCUMENTS

| | | | |
|---|---|---|---|
| 3,593,023 A | 7/1971 | Dodson et al. | |
| 3,696,247 A | 10/1972 | McIntosh et al. | |
| 3,743,426 A | 7/1973 | Steinberg | |
| 3,908,167 A | 9/1975 | Hulls et al. | |
| 3,957,372 A | 5/1976 | Jowett et al. | |
| 3,958,122 A | 5/1976 | Jowett et al. | |
| 3,973,848 A | 8/1976 | Jowett et al. | |
| 3,979,589 A * | 9/1976 | Sternberg et al. | 250/252.1 |
| 4,160,373 A | 7/1979 | Fastaia et al. | |

(Continued)

FOREIGN PATENT DOCUMENTS

WO    WO 98/37405    8/1998

OTHER PUBLICATIONS

Technical Proposal—"Vehicle Inspection Instrumentation"; submitted to California Air Resources Board: Sep. 1, 1971, Lockheed Palo Alto Research Laboratory, Lockheed Missiles & Space Company—A Group Division of Lockheed Aircraft Corporation, Palo Alto, California.

(Continued)

*Primary Examiner*—Michael Cygan
(74) *Attorney, Agent, or Firm*—Pillsbury Winthrop Shaw Pittman LLP

(57) ABSTRACT

A remote emissions sensing system is provided with $NO_x$ detection capability. First, a reading of the ambient $NO_x$ concentration is taken just prior to each vehicle passing through the system. This measurement accounts for any ambient $NO_x$ concentration that may be lingering from the exhaust of a previous vehicle. Next, the system takes a blocked reading when the vehicle is located in the path of the beam. This reading accounts for any ambient or system noise that may exist. Finally, the system takes a reading of the exhaust plume as the beam passes through the plume. A processor determines the portion of the reading due to the exhaust plume by subtracting the ambient and blocked readings from the exhaust plume reading. As a result, a more accurate exhaust concentration reading is provided. Additionally, the system may process exhaust plume readings only in a predetermined wavelength band associated with the known absorption spectrum of $NO_x$ so that data points for which there is no significant absorption of $NO_x$ may be eliminated. Thus, any noise or other interference in the non-absorptive wavelengths are minimized. Also, changes in the intensity of the radiation are compensated by subtracting a baseline intensity from each signal.

16 Claims, 1 Drawing Sheet

WAVELENGTH

U.S. PATENT DOCUMENTS

| | | | |
|---|---|---|---|
| 4,390,785 A | 6/1983 | Faulhaber et al. |
| 4,480,191 A | 10/1984 | Karpowycz |
| 4,490,043 A | 12/1984 | Cramp |
| 4,544,273 A | 10/1985 | Berndt |
| 4,560,873 A | 12/1985 | McGowan et al. |
| 4,663,961 A | 5/1987 | Nelson et al. |
| 4,719,360 A | 1/1988 | Kontani et al. |
| 4,746,218 A | 5/1988 | Lord, III |
| 4,765,961 A | 8/1988 | Schiff et al. |
| 4,795,253 A | 1/1989 | Sandridge et al. |
| 4,810,884 A | 3/1989 | Carlson |
| 4,818,705 A | 4/1989 | Schneider et al. |
| 4,829,183 A | 5/1989 | McClatchie et al. |
| 4,924,095 A | 5/1990 | Swanson, Jr. |
| 4,990,780 A | 2/1991 | Lee et al. |
| 4,999,498 A | 3/1991 | Hunt et al. |
| 5,060,505 A | 10/1991 | Tury et al. |
| 5,099,680 A | 3/1992 | Fournier et al. |
| 5,105,651 A | 4/1992 | Gutmann |
| 5,129,257 A | 7/1992 | Carduner et al. |
| 5,184,017 A | 2/1993 | Tury et al. |
| 5,210,702 A | 5/1993 | Bishop et al. |
| 5,246,868 A | 9/1993 | Busch et al. |
| 5,252,828 A | 10/1993 | Kert et al. |
| 5,306,913 A | 4/1994 | Noack et al. |
| 5,319,199 A | 6/1994 | Stedman et al. |
| 5,327,356 A | 7/1994 | Lang et al. |
| 5,332,901 A | 7/1994 | Eckles et al. |
| 5,343,043 A | 8/1994 | Johnson |
| 5,371,367 A | 12/1994 | DiDomenico et al. |
| 5,373,160 A | 12/1994 | Taylor |
| 5,386,373 A | 1/1995 | Keeler et al. |
| 5,401,967 A | 3/1995 | Stedman et al. |
| 5,418,366 A | 5/1995 | Rubin et al. |
| 5,451,787 A | 9/1995 | Taylor |
| 5,479,255 A | 12/1995 | Denny et al. |
| 5,489,777 A | 2/1996 | Stedman et al. |
| 5,498,872 A | 3/1996 | Stedman et al. |
| 5,572,424 A | 11/1996 | Kellogg et al. |
| 5,583,765 A | 12/1996 | Kleehammer |
| 5,589,629 A | 12/1996 | Quinn |
| 5,591,975 A * | 1/1997 | Jack et al. ............... 250/338.5 |
| 5,621,166 A | 4/1997 | Butler |
| 5,644,133 A | 7/1997 | Didomenico et al. |
| 5,693,872 A | 12/1997 | Quinn |
| 5,719,396 A | 2/1998 | Jack et al. |
| 5,726,450 A | 3/1998 | Peterson et al. |
| 5,731,510 A | 3/1998 | Jones et al. |
| 5,753,185 A | 5/1998 | Mathews et al. |
| 5,831,267 A | 11/1998 | Jack et al. |
| 6,396,056 B1 | 5/2002 | Lord et al. |

OTHER PUBLICATIONS

Hoshizaki, et al., Final Report—"Vehicle Inspection Instrumentation"; submitted to California Air Resources Board; Jun. 1973, Lockheed Palo Alto Research Laboratory, Lockheed Missiles & Space Company—A Group Division of Lockheed Aircraft Corporation, Palo Alto, California.

http://www.epa.gov/otag/15-remot.htm; "Remote Sensing: A Supplemental Tool for Vehicle Emission Control," Aug. 1993, EPA 400-F-92-017, Fact Sheet OMS-15; 4 pages.

Lucien W. Chaney, "The Remote Measurement of Traffic Generated Carbon Monoxide, APCA Note-Book," Journal of the Air Pollution Association; Copyright 1983; 3 pages.

Paul Stockwell, "Tunable Diode Laser Systems Break New Ground in Water Vapour Analysis"; IMA Ltd., Unit Newall Hall Park, Otley, West Yorkshire, United Kingdom; [undated]; 8 pages.

Mark G. Allen, "Diode Laser Absorption Sensors for Gas Dynamic and Combustion Flows," Copyright 1998 Measurement Science and Technology 9; 61 pages.

Kerry L. Swayne, "Infrared Remote Sensing of On-Road Motor Vehicle Emissions in Washington State," Mar., 1999, Air Quality Program, Washington State Department of Ecology, Washington; Publication #99-204; 20 pages.

Gary A. Bishop, et al., "IR Long-Path Photometry: A Remote Sensing Tool for Automobile Emissions," 1989; reprinted from Analytical Chemistry, 61. 671A; 1989; 6 pages.

Gary A. Bishop, et al., "Oxygenated Fuels, A Remote Sensing Evaluation," SAE Technical Paper Series; Copyright 1989 Society of Automotive Engineers, Inc.; 7 pages.

Robert D. Stephens, "Remote Sensing Data and a Potential Model of Vehicle Exhaust Emissions," Nov. 1994, vol. 44, Journal of Air & Waste Management Association, pp. 1284-1292.

"An Analysis of On-Road Remote Sensing as a Tool for Automobile Emissions Control," Final Report Prepared by University of Denver Chemistry Department, Colorado, Mar. 1990; 174 pages; prepared for Illinois Department of Energy and Natural Resources.

Robert D. Stephens, et al., "Remote Sensing Measurements of In-Use Vehicle Carbon Monoxide and Hydrocarbon Exhaust Emissions," Environmental Science Department, Michigan, to be presented to Society of Automotive Engineers Government/Industry Meeting, Washington, D. C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug. 28, 1990, 30 pages; prepared by Sierra Research, Inc., California.

Robert D. Stephens, et al., "Remote Sensing Measurements of Carbon Monoxide Emissions from On-Road Vehicles," Copyright Jan. 1991, Air & Waste Management Association, vol. 42, No. 1, pp. 39-46.

Donald H. Stedman, et al., "Remote Sensing of On-Road Vehicle Emissions," Final Report to Coordinating Research Council, The University of Denver, Jan. 6, 1992, 21 pages.

Peter Popp, et al., "Development of a High-Speed Ultraviolet Spectrophotometer Capable of Real-Time NO and Aromatic Hydrocarbon Detection in Vehicle Exhaust," Department of Chemistry, University of Denver, Colorado, Prepared for Proceedings of the 7th CRC On-Road Vehicle Emissions Workshop, San Diego, California, Apr. 9-11, 1997; 10 pages.

John DiDomenico, et al., "Preliminary Results from Cold Start Sensor Testing," Presented to 7th CRC On-Road Vehicle Emissions Workshop, San Diego, California Apr. 9-11, 1997; 1 page.

Gary A. Bishop, et al., "Enhancements of Remote Sensing for Vehicle Emissions in Tunnels," Air & Waste Management Association, vol. 44, Feb. 1994, pp. 169-175.

Paul Leonard Guenther, "Contributions to On-Road Remote Sensing of Automobile Exhaust," A Thesis-Presented to the Faculty of Natural Sciences, Mathematics, and Engineering, University of Denver, Jun. 1992, 95 pages.

Donald H. Stedman, et al., "On-Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On-Road Emissions Measurement Systems Services," Prepared by Parsons Engineering Science, Inc., Pasadena, California, Sep. 1995.

"Proposal/Quote for Unstaffed On-Road Emissions Measurement Systems Services" in response to Phase IV—RFQ #94/95-003, prepared by Remote Sensing Technologies, Inc. delivered to Department of Consumer Affairs, Bureau of Automotive Repair, Sacramento, California, Sep. 1, 1995.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Dec. 9, 1997, prepared by General Motors R&D Center, Michigan; 20 pages.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.

Robert D. Stephens, et al., "Remote Sensing of Carbon Monoxide Emissions from On-Road Vehicles," Environemental Science Department, General Motors Research Laboratories, Michigan for presentation to Air and Waste Management Association, NC, May 1, 1990, 46 pages.

"Description and Documentation for Interim Vehicle Clean Screening Credit Utility," Draft Report, United States Environmental Protection Agency, May 1998, 40 pages.

David S. E. Petherick, "Ontario's Indoor, Controlled-Mode Remote Sensing I/M Prescreen Concept," Ministry of Transportation of Ontario, Copyright 1996 Society of Automotive Engineers, Inc., 9 pages.

P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.

"On Road Emissions Measurement Systems—Specifications," Bureau of Automotive Repair, Aug. 30, 1999, Revision—J, 15 pages.

Craig S. Rendahl, "Further Analysis of Wisconsin's Remote Vehicle Emissions Sensing Feasibility Studies," "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, May 1996, 34 pages.

James D. Peterson, et al., "Find and Fix the Polluters", Chemtech, Jan. 1992, Copyright 1992 Americam Chemical Society, 7 pages.

RSD 1000 Operator's Manual (Preliminary), Remote Sensing Technologies, IFB No. 94019, Jun. 1993, 66 pages.

RSD-1000 Remote Sensing Device Information Package to Mr. Wolf Klassen, Department of Natural Resources, Presented by Dennis L. Smith, Feb. 24, 1993, 123 pages.

Robert D. Stephens, et al., "An Experimental Evaluation of Remote Sensing-Based Hydrocarbon Measurements: A Comparison to FID Measurements", Journal of the Air & Waste Management Association, vol. 46, Feb. 1996, pp. 148-158.

Donald H. Stedman, "Automobile Carbon Monoxide Emission", Environmental Science & Technology, vol. 23, No. 2, 1989, pp. 147-149.

Masayuki Adachi, et al., "Automotive Emission Analyses Using FTIR Spectrophotometer", Published by the Society of Automotive Engineers, SAE#920723, pp. 820-827.

Michael D. Koplow, et al., "Characterization of On-Road Vehicle NO Emissions by Means of a TILDAS Remote Sensing Instrument", Published by the Coordinating Research Council, Published for the 7$^{th}$ CRC On-Road Vehicle Emissions Workshop, Mar. 11, 1997, pp. 1-25.

Scott E. McLaren, et al., "Comparison of an Open Path UV and FTIR Spectrophotometer", Published by the Air & Waste Management Association, Published for Presentation at the 85$^{th}$ Annual Meeting & Exhibition, Kansas City, Missouri, Jun. 21-26, 1992, pp. 1-10.

"Developing an Inspection/Maintenance Program for Alternatively-Fueled Vehicles". Third Interim Report Submitted to the California Bureau of Automotive Repair, Submitted by Radian Corporation, Apr. 20, 1993, 147 pages.

Iain Frederick Mcvey, "Development of a Remote Sensor for Mobile Source Nitric Oxide", A Thesis Presented to the Faculty of Natural Sciences, Mathematics, and Engineering, University of Denver, Nov. 1992, 111 pages.

S. P. Beaton, et al., "Emission Characteristics of Mexico City Vehicles", Journal of the Air & Waste Management Association, vol. 42, No. 11, Nov. 1992, pp. 1424-1429.

Douglas R. Lawson, et al., "Emissions from In-Use Motor Vehicles in Los Angeles: A Pilot Study of Remote Sensing and the Inspection and Maintenance Program", Journal of the Air & Waste Management Association, vol. 40, No. 8, Aug. 1990, pp. 1096-1105.

Yi Zhang, et al., "Enhancement of Remote Sensing for Mobile Source Nitric Oxide", Journal of the Air & Waste Management Association, vol. 46, Jan. 1996, pp. 25-29.

Donald H. Stedman, et al., "Evaluation of a Remote Sensor for Mobile Source CO Emissions", U.S. Environmental Protection Agency, CR-815778-01-0, Report No. EPA/600/4-90/032, Jan. 1991, 90 pages.

James Butler, et al., "Factors Affecting the NDIR Measurement of Exhaust Hydrocarbons", Published by the Coordinating Research Council, Published for the CRC 5$^{th}$ On-Road Vehicle Emissions Workshop, 1995, 16 pages.

Scott E. McLaren, et al., "Flux Measurements Using Simultaneous Long Path Ultraviolet and Infrared Spectroscopy", Published by the Air & Waste Management Association, Published for Presentation at the 83$^{rd}$ Annual Meeting & Exhibition, Pittsburgh, Pennsylvania, Jun. 24-29, 1990, 7 pages.

Gary A. Bishop, et al., "Infrared Emission and Remote Sensing", Journal of the Air & Waste Management Association, vol. 42, No. 5, May 1992, pp. 695-697.

Hakan Axelsson, et al., "Measurement of Aromatic Hydrocarbons with the DOAS Technique", Applied Spectroscopy, vol. 49, No. 9, 1995, pp. 1254-1260.

Gary A. Bishop, et al., "Method Comparisons of Vehicle Emissions Measurements in the Fort McHenry and Tuscarora Mountain Tunnels", Atmospheric Environment, vol. 30, No. 12, 1996, pp. 2307-2316.

Donald H. Stedman, et al., "NOx Data by Remote Sensing", Published by the Coordinating Research Council, Published for the 5$^{th}$ CRC On-Road Vehicle Emissions Workshop, Apr. 3-5, 1995, 16 pages.

Donald H. Stedman, et al., "On-Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE-AQ-91/14, Oct. 1991, pp. 1-70.

Gary A. Bishop, et al., "On-Road Carbon Monoxide Emission Measurement Comparisons for the 1988-1989 Colorado Oxy-Fuels Program", *Environmental Science & Technology*, vol. 24, No. 6, 1990, pp. 843-847.

Donald H. Stedman, et al., "On-Road CO Remote Sensing in the Los Angeles Basin", Final Report Prepared for the Research Division, California Air Resources Board, Submitted by University of Denver Chemistry Department, Aug. 1991, Contract No. A932-189, 70 pages.

Scott McLaren, "Open Path Spectrometers for Atmospheric Monitoring", A Dissertation Presented to the Faculty of Natural Sciences, Mathematics and Engineering, Nov. 1995, 170 pages.

Carol E. Lyons, et al., "Remote Sensing Enhanced Motor Vehicle Emissions Control for Pollution Reduction in the Chicago Metropolitan Area: Siting and Issue Analysis", Final Report Prepared by University of Denver Atmospheric Science Center, Prepared for Illinois Department of Energy and Natural Resources, Office of Research and Planning, Illinois Contract AQ 30, Project 90/009, Report No. ILENR./RE-AQ-91/15, Oct. 1991 pp. 1-65.

Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.

Brett C. Singer, et al., "Scaling of Infrared Remote Sensor Hydrocarbon Measurements for Motor Vehicle Emission Inventory Calculations", *Environmental Science & Technology*, vol. 32, No. 21, 1998, pp. 3241-3248.

Lucian W. Chaney, "The Remote Measurement of Traffic Generated Carbon Monoxide", *Journal of the Air Pollution Control Association*, vol. 33, No. 3, Mar. 1983, pp. 220-222.

Jose Luis Jimenez-Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.

"Vehicle Inspection Instrumentation", Published by the Lockheed Missiles and Space co., Inc., Report No. ARB-R 643-73-26, Jun. 30, 1973, 99 pages.

John E. Sibsby, Jr., et al., "Volatile Organic Compound Emissions from 46 In-Use Passenger Cars", *Environmental Science & Technology*, vol. 21, No. 5, 1987, pp. 466-475.

Yi Zhang, et al., "Worldwide On-Road Vehicle Exhaust Emissions Study by Remote Sensing", *Environmental Science & Technology*, vol. 29, No. 9, 1995, pp. 2286-2294.

* cited by examiner 326 nm

WAVELENGTH

WAVELENGTH

REMOTE EMISSIONS SENSING SYSTEM WITH IMPROVED $NO_x$ DETECTION

This application is a continuation of application Ser. No. 09/520,166, filed Mar. 7, 2000, now abandoned.

This application is a continuation of application Ser. No. 09/398,199, filed Sep. 17, 1999, now abandoned which claims priority to Provisional Application Ser. No. 60/100,913 filed Sep. 17, 1998.

FIELD OF THE INVENTION

Remote emissions sensing system and method with improved nitrous oxide ($NO_x$) detection, including processing to account for the presence of ambient $NO_x$.

BACKGROUND OF THE INVENTION

Remote emissions sensing systems generally are known. One such system comprises a source of electromagnetic radiation arranged to pass a beam of radiation through the exhaust plume of a motor vehicle as the motor vehicle passes by the system, and one or more detectors arranged to receive the radiation after it passes through the exhaust plume of the vehicle. A filter may be associated with one or more detectors to enable the detector to determine the intensity of electromagnetic radiation having a particular wavelength or range of wavelengths. The wavelengths may be conveniently selected to correspond to wavelengths absorbed by molecular species of interest in an exhaust plume (e.g., HC, CO, CO2, $NO_x$, or other molecular species). The one or more detector output voltages that represent the intensity of the electromagnetic (em) radiation measured by that detector. The voltages are input to a processor. The processor calculates the difference between the known intensity of the light source and the intensity detected by the detectors to determine the amount of absorption by particular molecular species (based on predetermined wavelengths associated with that species). Based on the measured absorption(s), the concentration of one or more molecular species in the emissions may be determined in a known manner. For various reasons, inaccuracies can occur when remotely sensing emissions.

Some remote emission sensing systems do not have the capability to detect $NO_x$. Other systems detect $NO_x$, but suffer from various drawbacks. One problem is that when detecting the $NO_x$ concentration present in an exhaust plume, the presence of ambient $NO_x$ can adversely affect the accuracy of the detected concentration. For example, if two cars pass a test station within a relatively short time period, $NO_x$ emissions from the first car may linger and be mixed with the exhaust plume of the second car thereby skewing the measurement of $NO_x$ concentration of the second car. Other sources of ambient $NO_x$ may lead to a similar result.

A second problem arises, due to variations in light source intensity. Generally, to detect the $NO_x$ concentration in an exhaust plume, the output of a detector adapted to determine the amount of absorption of the light beam due to the presence of $NO_x$ is compared to a value indicative of the intensity of the light source, with the difference representing the amount of absorption due to the presence of $NO_x$.

Typically, a standard value is used for the light source intensity. However, variations in the actual intensity of the source can cause inaccuracies in the detected amount of $NO_x$. A third problem arises due to the presence of noise. Other problems and drawbacks exist.

SUMMARY OF THE INVENTION

One object of the invention is to overcome these and other limitations, problems and drawbacks of prior systems and methods.

Another object of the present invention is to increase the reliability and accuracy of $NO_x$ readings taken in a remote emissions sensing system.

Another object of the invention is to improve the accuracy of $NO_x$ emissions readings by accounting for the presence of ambient $NO_x$.

Another object of the invention is to improve the accuracy of $NO_x$ emissions readings by accounting for the presence of ambient noise.

It is another object of the invention to improve the processing efficiency of $NO_x$ concentration calculations.

These and other objects of the invention are accomplished according to various embodiments of the present invention. According to one embodiment of the present invention a remote emissions sensing system is provided with $NO_x$ detection capability. Ideally, the $NO_x$ detected is the $NO_x$ present in the exhaust plume emanating from a motor vehicle being tested. To account for ambient $NO_x$ (for example, from a previous car), for each vehicle whose exhaust is measured, an ambient $NO_x$ concentration reading is taken. Preferably, a "blocked" beam reading is also taken prior to exhaust plume measurement. The ambient and blocked beam readings are both subtracted from the exhaust plume reading to render a more accurate exhaust concentration reading.

Additionally, the system may be configured to process exhaust plume readings only in a predetermined wavelength band associated with the known absorption spectrum of $NO_x$.

The above and other objects, features and advantages of the present invention will be better understood from the following detailed description of the invention.

DETAILED DESCRIPTION OF THE INVENTION

Figure 1:
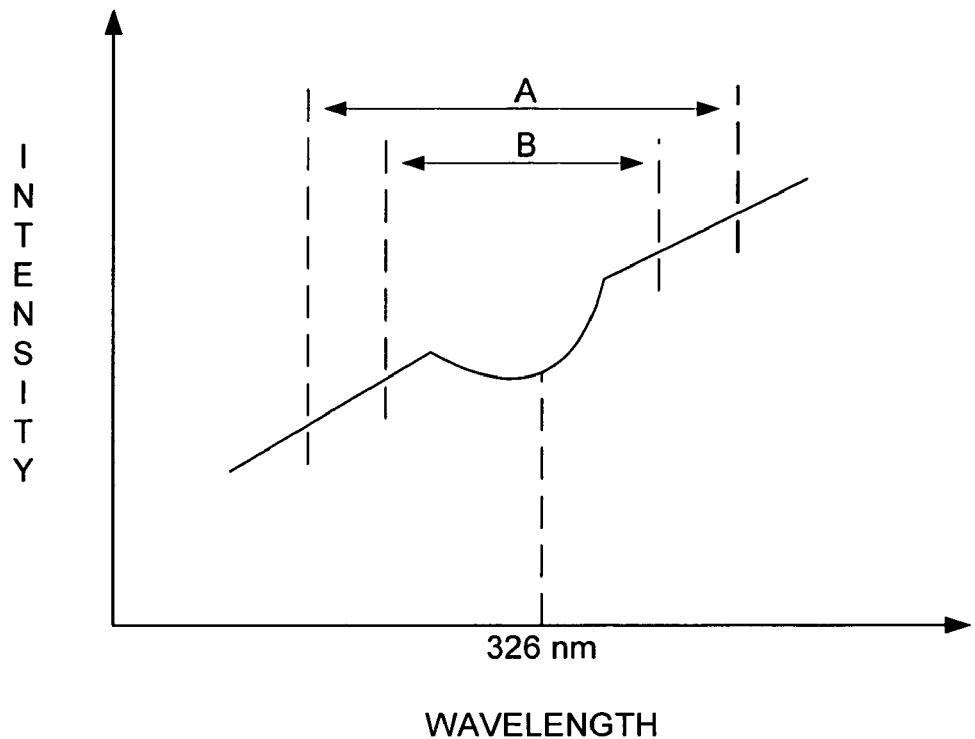
FIG. 1 depicts a schematic representation of intensity versus wavelength data for one embodiment of the invention.

According to one embodiment, the emissions detection may be performed by a remote sensing device, such as RSD-1000 or RSD-2000, manufactured by RSTi. Tucson. Ariz.

Typically, the remote sensing device and analyzer system includes at least one source of radiation (e.g., infrared (IR), ultra-violet (UV), etc.), at least one detector of radiation, and a processor to process the detected radiation signals. According to one embodiment of the invention, the radiation emitted by the source(s) may be directed across a roadway along a predetermined path. In some embodiments, additional optics or beam directing devices may be used to re-direct the beam of radiation. Ultimately, the source radiation is received by the detector(s). Other system configurations may also be used. When a vehicle passes along roadway, the source beam(s) may pass through an exhaust plume of the vehicle.

The detector(s) record the presence of various exhaust constituents (e.g., HC, $CO_2$, CO, $NO_x$, etc.), typically, by recording a voltage level indicative of the amount of absorption of the source beam. The processor, in part, performs an analysis of the plume to analyze the exhaust emissions in a known manner.

According to one embodiment of the present invention, the remote emission detector (RSD) system takes a reading of the ambient $NO_x$ concentration present just prior to each vehicle passing through the system. As the vehicle is passing through the system, the RSD system takes a "blocked" reading (i.e., a reading when the vehicle is located in the path of the beam between the source and detector). This reading may reflect any ambient or system noise which may be present. The RSD system also takes a reading of the exhaust plume as the beam passes through the plume. Thus, in accordance with a one embodiment of the present invention, for each vehicle whose $NO_x$ reading is to be taken, at least three measurements are made, including an ambient concentration reading, a "blocked" reading and an exhaust plume reading. Since the ambient concentration and noise can vary from test to test, detecting the ambient $NO_x$ concentration and noise for each test can permit more accurate and reliable $NO_x$ concentration determinations to be made.

Each of the readings is made by one or more detectors. The outputs of the detector(s), reflecting the ambient $NO_x$ reading, the blocked beam reading and the exhaust plume reading (and other desired data), are provided to a processor. The processor determines the ambient concentration of $NO_x$ and the concentration of $NO_x$ from the exhaust plume and subtracts the ambient concentration from the $NO_x$ concentration from the plume for each vehicle tested. Preferably, the blocked beam reading for each vehicle is subtracted from the exhaust plume reading for that vehicle to remove ambient and or system noise to further improve the accuracy and or reliability of the test results.

Each of the readings and the process and system for obtaining reliable $NO_x$ readings in connection with a remote sensing system will now be discussed in more detail. Initially, as the vehicle approaches the light beam, the baseline ambient concentration reading is taken. In connection with this step the detector measures the ambient $NO_x$ concentration just prior to the vehicle's entry into and through the light beam. The baseline ambient concentration readings may be scheduled to occur periodically when no vehicle or emissions source is within detection range. Thus, the most recent reading for ambient concentration may be stored and used in connection with the concentration calculation for each vehicle. Alternatively, a trigger event may cause the RSD system to take the ambient concentration reading. In either case, the readings are preferably obtained by taking a plurality of samples at short intervals over a predetermined measurement interval. For example, an ambient reading may comprise 50 samples at 10 ms. intervals over a 0.5 second measurement interval.

Once a vehicle breaks the light beam, a "blocked" reading or "dark current" reading, may be performed. This reading measures baseline current and noise in the system. The baseline values may change during the course of the day as it is dependent upon, for example, ambient temperature. The "blocked" reading is taken for each vehicle for which an $NO_x$ reading is desired. Preferably, the blocked reading is taken after the ambient concentration reading but prior to the exhaust plume reading. The exhaust plume reading is taken based upon the actual emissions from each vehicle to be measured, in a known manner.

One embodiment of the present invention incorporates certain data processing routines conveniently chosen to increase the accuracy and validity of resulting $NO_x$ concentrations. FIG. 1 depicts a typical data plot that may result from an absorption measurement of $NO_x$. The Y axis contains radiation intensity values and the X axis contains radiation wavelength values. An absorption of radiation will typically appear as a dip in the signal at particular wavelengths. For example, absorption of NO will typically occur centered substantially around wavelengths of 326 nm. In a known manner, exhaust emission data is typically normalized or ratioed by comparison with another exhaust constituent (e.g., $CO_2$). Certain existing systems may ratio using data corresponding to a range of wavelengths indicated by bracket A on FIG. 1. As can be seen, this range includes many data points for which there is no significant absorption of $NO_x$. Thus, any noise or other inaccuracies present in these non-absorptive wavelengths may lead to erroneous results in determining the concentration of $NO_x$ in the exhaust emissions. The present invention reduces errors of this sort by selecting a convenient range of wavelengths over which to ratio. For example, as shown in FIG. 1, a range of wavelengths, indicated by bracket B and substantially centered around an absorption dip may be used to calculate a ratio.

Figure 2:
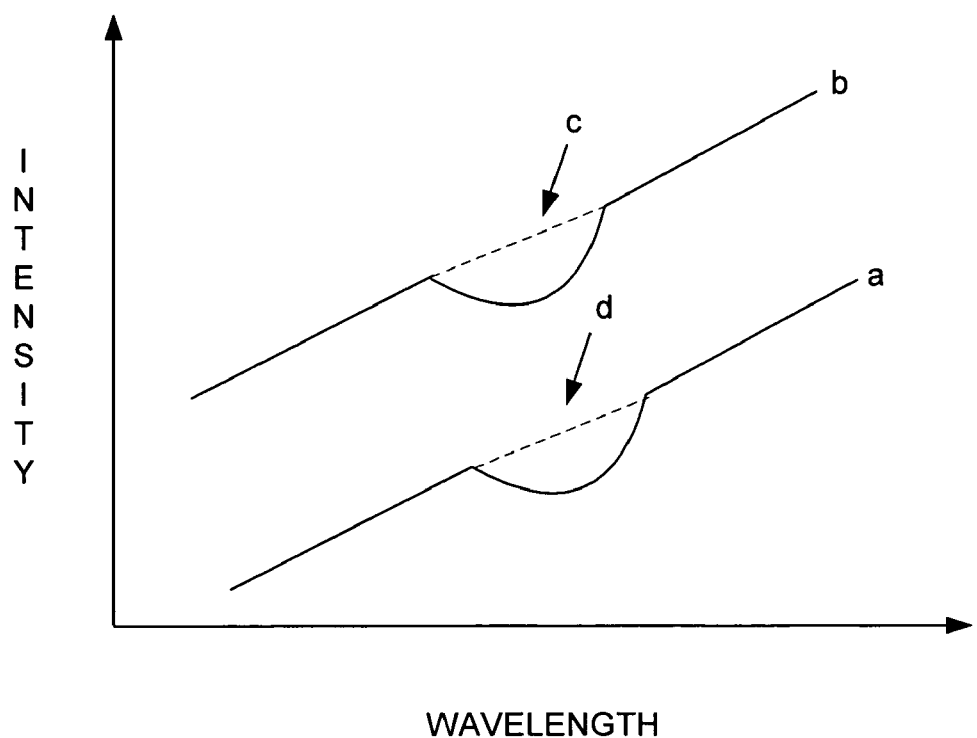
FIG. 2 depicts a schematic representation of intensity versus wavelength data for another one embodiment of the invention.

The present invention also compensates for changes in the intensity of the radiation to calculate a more accurate $NO_x$ concentration. FIG. 2 depicts two absorption signals (indicated as "a" and "b" in FIG. 2) for two measurements of $NO_x$ concentration. The apparent shift in the curves may be caused by a variety of reasons. For example, as ambient conditions (e.g., air temperature, humidity, etc.) change, the intensity may also change and cause a shift in the detected signal. The present invention compensates for such an effect by subtracting a baseline intensity from each signal. The baseline intensity may be calculated by a variety of methods. For example, a substantially linear region (indicated as "c" and "d" on FIG. 2) may be used to obtain a baseline intensity level. Thus, each measurement will preferably have a baseline corresponding to the identical conditions during which the measurement was taken and a more accurate determination of $NO_x$ concentration may be calculated.

Other embodiments and uses of the invention will be apparent to those skilled in the art from consideration of the specification and practice of the invention disclosed herein. The specification and examples should be considered exemplary only.

We claim:

1. A method for determining the concentration of $NO_x$ in an exhaust plume of a vehicle passing through a beam of radiation projected along an optical path between a radiation source having an initial intensity, and a detector for measuring intensities of radiation incident upon the detector over a range of wavelengths, the method comprising:

measuring, under ambient conditions, intensities of radiation over a range of wavelengths to determine ambient $NO_x$ concentration, wherein the range of wavelengths includes at least one absorption wavelength for $NO_x$;

measuring intensities of radiation, over the range of wavelengths, while the beam of radiation is passing through an exhaust plume of a vehicle after the vehicle passes through the optical path;

determining a baseline intensity by interpolating a substantially linear region over an absorption dip in an absorption curve generated from the intensities measured while the beam of radiation is passing through the exhaust plume of the vehicle;

calculating the concentration of $NO_x$ in the exhaust plume of the vehicle, wherein calculating the concentration of $NO_x$ includes using the baseline intensity to compensate for changes in the initial intensity; and subtracting the ambient $NO_x$ concentration from the concentration of $NO_x$ in the exhaust plume of the vehicle.

2. The method of claim 1, wherein the measuring of intensities of radiation under ambient conditions occurs at predetermined intervals.

3. The method of claim 1, wherein the measuring of intensities of radiation under ambient conditions is initiated upon an occurrence of a predetermined trigger event.

4. The method of claim 1, further comprising:

taking a blocked beam reading when the vehicle is in the optical path and blocking the beam of radiation, wherein the blocked beam reading measures basline current or noise.

5. The method of claim 4, furter comprising:

substracting the blocked beam reading from the concentration of NOx in the exhaust plume.

6. The method of claim 4, wherein the blocked beam reading is taken after the measuring of intensities of radiation under ambient conditions, but before the measuring of intensities of radiation while the beam of radiation is passing through the exhaust plume of the vehicle.

7. The method of claim 4, wherein the measuring of intensities of radiation under ambient conditions occurs prior to taking the blocked beam reading.

8. The method of claim 1, wherein the range of wavelengths is selected to be substantially centered around a characteristic wavelength such that a number of data points for which there is no signficant $NO_x$ absorption is minimized.

9. A system for determining the concentration of $NO_x$ in an exhaust plume of a vehicle passing through a beam of radiation projected along an optical path between a radiation source having an initial intensity, and a detector for measuring intensities of radiation incident upon the detector over a range of wavelengths, the system comprising:

means for measuring, under ambient conditions, intensities of radiation over a range of wavelengths to determine ambient $NO_x$ concentration, wherein the range of wavelengths includes at least one absorption wavelength for $NO_x$;.

means for measuring intensities of radiation, over the range of wavelengths, while the beam of radiation is passing through an exhaust plume of a vehicle after the vehicle passes through the optical path;

means for determining a baseline intensity by interpolating a substantially linear region over an absorption dip in an absorption curve generated from the intensities measured while the beam of radiation is passing through the exhaust plume of the vehicle;

means for calculating the concentration of $NO_x$ in the exhaust plume of the vehicle, wherein calculating the concentration of $NO_x$ includes using the baseline intensity to compensate for changes in the initial intensity; and means for subtracting the ambient $NO_x$ concentration from the concentration of $NO_x$ in the exhaust plume of the vehicle.

10. The system of claim 9, wherein the measuring of intensities of radiation under ambient conditions occurs at predetermined intervals.

11. The system of claim 9, wherein the measuring of intensities of radiation under ambient conditions is initiated upon an occurrence of a predetermined trigger event.

12. The system of claim 9, further comprising:

means for taking a blocked beam reading when the vehicle is in the optical path and blocking the beam of radiation, wherein the blocked beam reading measures baseline current or noise.

13. The system of claim 12, further comprising:

means for subtracting the blocked beam reading from the concentration of $NO_x$ in the exhaust plume.

14. The system of claim 12, wherein the blocked beam reading is taken after the measuring of intensities of radiation under ambient conditions, but before the measuring of intensities of radiation while the beam of radiation is passing through the exhaust plume of the vehicle.

15. The system of claim 12, wherein the measuring of intensities of radiation under ambient conditions occurs prior to taking the blocked beam reading.

16. The system of claim 9, wherein the range of wavelengths is selected to be substantially centered around a characteristic wavelength such that a number of data points for which there is not significant $NO_x$ absorption is minimized.

* * * * *